United States Patent
Mahler

(10) Patent No.: US 8,066,899 B2
(45) Date of Patent: Nov. 29, 2011

(54) NON-IGNITABLE GASEOUS COMPOSITION COMPRISING DIFLUOROMETHANE AND TETRAFLUOROETHYLENE

(75) Inventor: Barry Asher Mahler, Glen Mills, PA (US)

(73) Assignee: E.I. du Pont de Nemours and Company, Wilmington, DE (US)

( * ) Notice: Subject to any disclaimer, the term of this patent is extended or adjusted under 35 U.S.C. 154(b) by 285 days.

(21) Appl. No.: 12/439,565

(22) PCT Filed: Sep. 4, 2007

(86) PCT No.: PCT/US2007/019351
§ 371 (c)(1),
(2), (4) Date: Mar. 25, 2009

(87) PCT Pub. No.: WO2008/027603
PCT Pub. Date: Mar. 6, 2008

(65) Prior Publication Data
US 2010/0012900 A1  Jan. 21, 2010

Related U.S. Application Data

(60) Provisional application No. 60/842,120, filed on Sep. 1, 2006.

(51) Int. Cl.
C09K 5/04 (2006.01)
(52) U.S. Cl. .......................................... 252/67; 252/68
(58) Field of Classification Search ................ 252/67, 252/68
See application file for complete search history.

(56) References Cited

U.S. PATENT DOCUMENTS

| 5,162,594 A | 11/1992 | Krespan |
| 6,184,426 B1 | 2/2001 | Belen'Kill et al. |
| 2003/0013618 A1 * | 1/2003 | Abramowski et al. ........ 508/181 |
| 2008/0281067 A1 * | 11/2008 | Nanba et al. ................ 526/255 |

FOREIGN PATENT DOCUMENTS

| DE | 1206424 | | 12/1965 |
| EP | 0915074 A1 | | 5/1999 |
| JP | 55111425 | | 8/1980 |
| JP | 05239450 A | * | 9/1993 |
| WO | 9429250 A1 | | 12/1994 |

OTHER PUBLICATIONS

Anonymous, RD-418030 A, Feb. 10, 1999, Derwent, Front Page.*
M. M. Renfrew et al., Polytetrafluoroethylene. Heat-Resistant, Chemically Inert Plastic, Industrial and Engineering Chemistry, 1946, vol. 38:870-877.
J. Lee et al., Vapor-Liquid Equilibria for Hydrogen Fluoride and Difluoromethane, 1,1,1,12-Tetrafluoroethane, and + 1-Chloro-1,2,2,2-Tetrafluoroethane at 283.3 and 298.2 K, J. Chem. Eng. Data, 1996, vol. 41:43-46.
Tetrafluoroethylene Liquid and Vapor Mixtures for Safe Shipping and Handling, Research Disclosure, Mason Publications, 1999, No. 418, p. 194.

* cited by examiner

Primary Examiner — Gregory Webb

(57) ABSTRACT

The present disclosure relates to non-ignitable gaseous compositions comprising difluoromethane and tetrafluoroethylene. When the pressure is at least 150 psig, the molar percentage of tetrafluoroethylene in the non-ignitable gaseous composition is no more than 111.6−0.124X. When the pressure is less than 150 psig, the molar percentage of tetrafluoroethylene in the non-ignitable gaseous composition is no more than 102−0.06X. X is the pressure in the unit of psig. The present disclosure also provides processes for making such non-ignitable gaseous compositions.
Also disclosed are azeotropic compositions of TFE and HFC-32.

13 Claims, 1 Drawing Sheet

Figure 1:
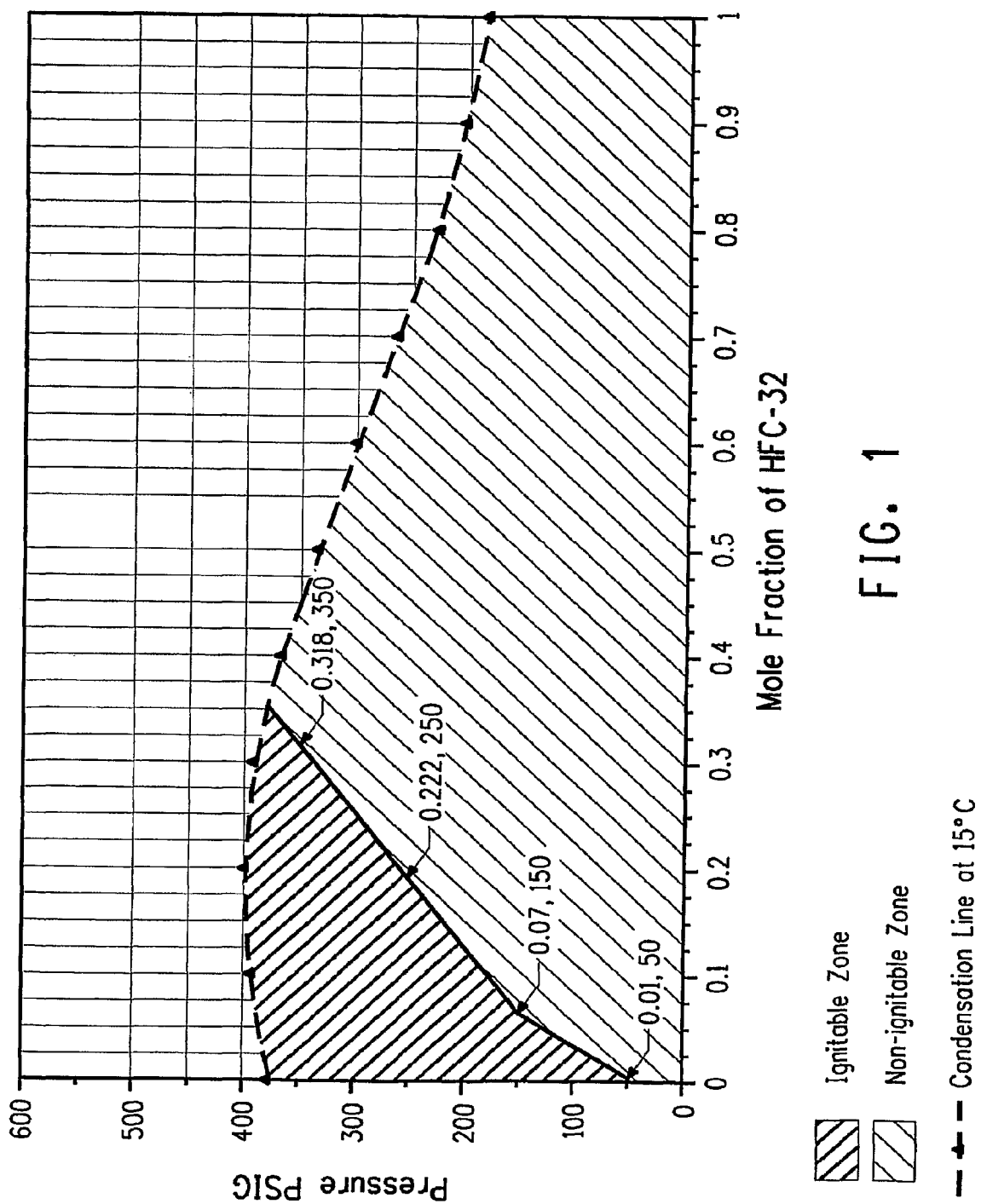

NON-IGNITABLE GASEOUS COMPOSITION COMPRISING DIFLUOROMETHANE AND TETRAFLUOROETHYLENE

BACKGROUND OF THE INVENTION

1. Field of the Disclosure

The present disclosure relates in general to a non-ignitable gaseous composition comprising difluoromethane (HFC-32) and tetrafluoroethylene (TFE). The present disclosure also relates in general to the processes for making non-ignitable gaseous compositions comprising HFC-32 and TFE.

2. Description of Related Art

Halogenated compounds, especially fluorinated compounds, such as fluorocarbons and hydrofluorocarbons, have been widely used in the industry as refrigerants, solvents, cleaning agents, foam blowing agents, aerosol propellants, heat transfer media, dielectrics, fire extinguishing agents, sterilants and power cycle working fluids, et al.

TFE ($CF_2=CF_2$) can be used as a starting material for making various fluorinated compounds, such as 1,1,1,2,2,3-hexafluoropropane (HFC-236cb). However, TFE is ignitable and explosive under certain conditions and poses danger towards industrial manufacturing processes utilizing TFE.

There is a need for a non-ignitable composition comprising TFE.

SUMMARY OF THE INVENTION

The present disclosure relates to non-ignitable gaseous compositions comprising difluoromethane and tetrafluoroethylene. When the pressure is at least 150 psig, the molar percentage of tetrafluoroethylene in the non-ignitable gaseous composition is no more than 111.6−0.124X. When the pressure is less than 150 psig, the molar percentage of tetrafluoroethylene in the non-ignitable gaseous composition is no more than 102−0.06X. X is the pressure in the unit of psig.

The present disclosure also provides processes for making such non-ignitable gaseous compositions.

The present disclosure also provides a composition comprising (a) TFE and (b) HFC-32; wherein the HFC-32 is present in an effective amount to form an azeotropic combination with the TFE.

The foregoing general description and the following detailed description are exemplary and explanatory only and are not restrictive of the invention, as defined in the appended claims.

BRIEF DESCRIPTION OF THE DRAWING(S)

Embodiments are illustrated in the accompanying figures to improve understanding of concepts as presented herein.

FIG. 1 includes as illustration of the non-ignitable and ignitable zone of the HFC-32 and TFE mixture.

Skilled artisans appreciate that objects in the figures are illustrated for simplicity and clarity and have not necessarily been drawn to scale. For example, the dimensions of some of the objects in the figures may be exaggerated relative to other objects to help to improve understanding of embodiments.

DETAILED DESCRIPTION OF THE INVENTION

Before addressing details of embodiments described below, some terms are defined or clarified.

The term "pre-mixing" is intended to mean mixing two or more chemical compounds prior to the catalytic reaction.

The term "condensation line" is intended to mean a pressure vs. composition curve at certain temperature, wherein the mixture will transform to the liquid state from the gaseous state above the pressure indicated by the curve.

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

Also, use of "a" or "an" are employed to describe elements and components described herein. This is done merely for convenience and to give a general sense of the scope of the invention. This description should be read to include one or at least one and the singular also includes the plural unless it is obvious that it is meant otherwise. As used herein, the term "non-ignitable" refers to the criteria from ASTM E 918-83 (Reapproved 1999), "Standard Practice for Determining Limits of Flammability of Chemicals at Elevated Temperature and Pressure", where "non-ignitable" is defined as exhibiting an increase in pressure (following a spark) of less than 7% of the initial absolute pressure. As an example, for an initial pressure of 364.7 psig, if the pressure increase following explosion is less than 26 psig, the gas or gas mixture is considered non-ignitable.

Unless otherwise defined, all technical and scientific terms used herein have the same meaning as commonly understood by one of ordinary skill in the art to which this invention belongs. Although methods and materials similar or equivalent to those described herein can be used in the practice or testing of embodiments of the present invention, suitable methods and materials are described below. All publications, patent applications, patents, and other references mentioned herein are incorporated by reference in their entirety, unless a particular passage is cited. In case of conflict, the present specification, including definitions, will control. In addition, the materials, methods, and examples are illustrative only and not intended to be limiting.

The present disclosure provides non-ignitable gaseous compositions comprising TFE and HFC-32 that are suitable for use in the production processes of fluorinated compounds. For example, such non-ignitable gaseous compositions can be used to produce $CF_3CF_2CH_2F$ (HFC-236cb) by following the procedures described in U.S. Pat. No. 6,184,426, hereby incorporated by reference.

The non-ignitable gaseous compositions in the present disclosure comprise TFE and HFC-32. When the pressure is at least 150 psig, the molar percentage of TFE in such gaseous compositions is no more than 111.6−0.124X. When the pressure is less than 150 psig, the molar percentage of TFE in such gaseous compositions is no more than 102−0.06X. In this disclosure, X is the pressure in the unit of psig. The pressure shall not exceed the one at the condensation line as indicated in FIG. 1. When the pressure goes above the condensation line, liquid phase will form.

In one embodiment of this invention, when the pressure is no more than 350 psig, non-ignitable gaseous compositions contain no more than 68.2 molar percent of TFE, and contain no catalysts.

In another embodiment of this invention, when the pressure is no more than 250 psig, non-ignitable gaseous compositions contain no more than 77.8 molar percent of TFE, and contain no catalysts.

In another embodiment of this invention, when the pressure is no more than 150 psig, non-ignitable gaseous compositions contain no more than 93 molar percent of TFE, and contain no catalysts.

In another embodiment of this invention, when the pressure is no more than 50 psig, non-ignitable gaseous compositions contain no more than 99 molar percent of TFE, and contain no catalysts.

Many aspects and embodiments have been described in this disclosure and are merely exemplary and not limiting. After reading this specification, skilled artisans appreciate that other aspects and embodiments are possible without departing from the scope of the invention.

Other features and benefits of any one or more of the embodiments will be apparent from the following detailed description, and from the claims.

In one embodiment of this invention, when the pressure is at 350 psig, a non-ignitable gaseous composition comprises 68.2 molar percent of TFE and 31.8 molar percent of HFC-32.

In another embodiment of this invention, when the pressure is at 250 psig, a non-ignitable gaseous composition comprises 77.8 molar percent of TFE and 22.2 molar percent of HFC-32.

In another embodiment of this invention, when the pressure is at 150 psig, a non-ignitable gaseous composition comprises 93 molar percent of TFE and 7 molar percent of HFC-32.

In another embodiment of this invention, when the pressure is at 50 psig, a non-ignitable gaseous composition comprises 99 molar percent of TFE and 1 molar percent of HFC-32.

Processes have been provided to pre-mix HFC-32 and TFE to form a non-ignitable gaseous mixture. There are a variety of methods for pre-mixing HFC-32 and TFE to form a non-ignitable gaseous mixture. For example, gaseous HFC-32 and TFE can be simply mixed together. When the pressure is at least 150 psig, the molar percentage of TFE in such mixture is no more than $111.6 - 0.124X$. When the pressure is less than 150 psig, the molar percentage of TFE in such mixture is no more than $102 - 0.06X$. In this disclosure, X is the pressure in the unit of psig. The pressure shall not exceed the one at the condensation line as indicated in FIG. 1. When the pressure goes above the condensation line, liquid phase will form.

The present disclosure also provides azeotrope or near azeotrope compositions comprising HFC-32 and TFE. An additional method for premixing and forming non-ignitable mixtures of HFC-32 and TFE is by forming an azeotrope or near azeotrope composition of HFC-32 and TFE.

As recognized in the art, an azeotrope or a near azeotrope composition is an admixture of two or more different components which, when in liquid form under a given pressure, will boil at a substantially constant temperature, which temperature may be higher or lower than the boiling temperatures of the individual components, and which will provide a vapor composition essentially identical to the liquid composition undergoing boiling.

For the purpose of this discussion, near azeotrope composition (also commonly referred to as an "azeotrope-like composition") means a composition that behaves like an azeotrope (i.e., has constant boiling characteristics or a tendency not to fractionate upon boiling or evaporation). Thus, the composition of the vapor formed during boiling or evaporation is the same as or substantially the same as the original liquid composition. Hence, during boiling or evaporation, the liquid composition, if it changes at all, changes only to a minimal or negligible extent. This is to be contrasted with non-near azeotrope compositions in which during boiling or evaporation, the liquid composition changes to a substantial degree.

Additionally, near azeotrope compositions exhibit dew point pressure and bubble point pressure with virtually no pressure differential. That is to say that the difference in the dew point pressure and bubble point pressure at a given temperature will be a small value. In this invention, compositions with a difference in dew point pressure and bubble point pressure of less than or equal to 3 percent (based upon the bubble point pressure) are considered to be near azeotropes.

Accordingly, the essential features of an azeotrope or a near azeotrope composition are that at a given pressure, the boiling point of the liquid composition is fixed and that the composition of the vapor above the boiling composition is essentially that of the boiling liquid composition (i.e., no fractionation of the components of the liquid composition takes place). It is also recognized in the art that both the boiling point and the weight percentages of each component of the azeotrope composition may change when the azeotrope or near azeotrope liquid composition is subjected to boiling at different pressures. Thus, an azeotrope or a near azeotrope composition may be defined in terms of the unique relationship that exists among the components or in terms of the compositional ranges of the components or in terms of exact weight percentages of each component of the composition characterized by a fixed boiling point at a specified pressure. Azeotrope compositions of TFE and HFC-32 comprise from about 87.1 mole percent to about 78.5 mole percent TFE and from about 12.9 mole percent to about 21.5 mole percent HFC-32, wherein the vapor pressure is from about 51.3 psig (348 kPa) to about 395 psig (2723 kPa) at a temperature of from about −50° C. to about 14° C.

Additionally, near azeotrope compositions containing TFE and HFC-32 may also be formed. Such near azeotrope compositions exist around azeotrope compositions. For example, a composition comprising 87.1 mole percent TFE and 12.9 mole percent HFC-32 is an azeotrope composition at −50° C. at 51.3 psig (348 kPa). Compositions comprising from about 100 mole percent to about 78.8 mole percent TFE and from about 0 mole percent to about 21.2 mole percent HFC-32 are near azeotrope compositions. Similarly, at 10° C. and 354 psig (2441 kPa), a composition comprising 79.7 mole percent TFE and 20.3 mole percent HFC-32 is an azeotrope composition, and compositions comprising from about 100 mole percent to about 64.6 mole percent TFE and from about 0 mole percent to about 35.4 mole percent HFC-32 are near azeotrope compositions.

Compositions may be formed that consist essentially of azeotrope combinations of TFE with HFC-32. These include compositions consisting essentially of from about 87.1 mole percent to about 78.5 mole percent TFE and from about 12.9 mole percent to about 21.5 mole percent HFC-32, wherein the vapor pressure is from about 51.3 psig (348 kPa) to about 395 psig (2723 kPa) at a temperature of from about −50° C. to about 14° C.

In one embodiment of this invention, an azeotrope composition of TFE and HFC-32 comprises about 86.1 mole percent TFE and about 13.9 mole percent HFC-32 which boils at −40° C. and 76.0 psig (524.1 kPa).

In another embodiment of this invention, an azeotrope composition of TFE and HFC-32 comprises about 85.2 mole percent TFE and about 14.8 mole percent HFC-32 which boils at −30° C. and 108.5 psig (748 kPa).

In another embodiment of this invention, an azeotrope composition of TFE and HFC-32 comprises about 84.1 mole percent TFE and about 15.9 mole percent HFC-32 which boils at −20° C. and 150.5 psig (1038 kPa).

In another embodiment of this invention, an azeotrope composition of TFE and HFC-32 comprises about 82.9 mole percent TFE and about 17.1 mole percent HFC-32 which boils at −10° C. and 203.7 psig (1405 kPa).

In another embodiment of this invention, an azeotrope composition of TFE and HFC-32 comprises about 81.5 mole percent TFE and about 18.5 mole percent HFC-32 which boils at 0° C. and 270 psig (1862 kPa).

In one embodiment of this invention, a non-ignitable gaseous mixture of HFC-32 and TFE has an azeotrope composition. Such a non-ignitable gaseous mixture can be formed by boiling a liquid phase of a HFC-32/TFE mixture to form the HFC-32/TFE azeotrope vapor phase.

For example, by maintaining a HFC-32/TFE mixture at about −7° C. and 205.8 psig (1419 kPa), an HFC-32/TFE azeotrope is formed that consists of about 17.4 mole percent HFC-32 and about 82.6 mole percent TFE. Such azeotropic composition is non-ignitable up to a pressure of about 225 psig (1552 kPa) and 30° C. This thus provides a method of producing non-ignitable compositions that can be stored or otherwise used in a process.

EXAMPLES

The concepts described herein will be further described in the following examples, which do not limit the scope of the invention described in the claims.

Legend

HFC-32 is difluoromethane ($CH_2F_2$)

TFE is tetrafluoroethylene ($CF_2\!=\!CF_2$)

Example 1

Example 1 demonstrates the ignitable and non-ignitable compositions at 150 psig.

The tests were performed in a horizontal 1.7 liter 316 stainless steel Nixon Reactor equipped with a 0-500 PSIG Dynisco strain gauge pressure transducer, 1/8" OD stainless steel tube injector, 2.5" long 20 gage Nichrome wire igniter, external electrical heater, and 1" diameter rupture disk with a 533 psi burst pressure. Gas mixtures were made up by partial pressure in the test vessel using the Peng-Robinson modification of the Redlich-Kwong equation of state to calculate mol. % from partial pressure (vol. %). Loading sequence was always arranged so that the major component was loaded after the minor component to increase the mixing efficiency of the injector.

Representative test results are shown in Table 1 below, and plotted in FIG. 1.

TABLE 1

| TFE Mol. % | HFC-32 Mol. % | Initial Press. (psig) | Initial Temp. (° C.) | Maximum Press. (psig) | Maximum Temp. (° C.) | |
|---|---|---|---|---|---|---|
| 20 | 80 | 150 | 30 | 152 | 31 | Non-Ignitable |
| 94 | 6 | 150 | 30 | >500 | 658 | Ignitable |
| 93 | 7 | 150 | 29 | 151 | 30 | Non-Ignitable |
| 93 | 7 | 150 | 29 | 151 | 30 | Non-Ignitable |
| 93 | 7 | 150 | 29 | 151 | 30 | Non-Ignitable |

Example 2

Example 2 demonstrates the ignitable and non-ignitable compositions at 250 psig.

The tests were performed using the same equipment and in the same way as described in Example 1 above.

Representative test results are shown in Table 2 below, and plotted in FIG. 1.

TABLE 2

| TFE Mol. % | HFC-32 Mol. % | Initial Press. (psig) | Initial Temp. (° C.) | Maximum Press. (psig) | Maximum Temp. (° C.) | |
|---|---|---|---|---|---|---|
| 79.6 | 20.4 | 250 | 29 | >500 | 317 | Ignitable |
| 77.8 | 22.2 | 250 | 29 | 253 | 31 | Non-Ignitable |
| 77.8 | 22.2 | 250 | 29 | 253 | 31 | Non-Ignitable |
| 77.8 | 22.2 | 250 | 30 | 253 | 31 | Non-Ignitable |

Example 3

Example 3 demonstrates a non-ignitable composition at 350 psig.

The test was performed using the same equipment and in the same way as described in Example 1 above. For the tests performed at 350 psig (and 30 deg. C.), ignitability was observed at 26.5 mol. % HFC-32 in TFE, and nonignitability in three tests at 31.8 mol. % HFC-32 in TFE.

Representative test results are shown in Table 3 below, and plotted in FIG. 1.

TABLE 3

| TFE Mol. % | HFC-32 Mol. % | Initial Press. (psig) | Initial Temp. (° C.) | Maximum Press. (psig) | Maximum Temp. (° C.) | |
|---|---|---|---|---|---|---|
| 68.2 | 31.8 | 353 | 30 | 359 | 32 | Non-Ignitable |

What is claimed is:

1. A non-ignitable gaseous composition consisting essentially of difluoromethane and tetrafluoroethylene, provided that when the pressure is at least 150 psig, the molar percentage of tetrafluoroethylene in said gaseous composition is no more than 111.6−0.124X, and that when the pressure is less than 150 psig, the molar percentage of tetrafluoroethylene in said gaseous composition is no more than 102−0.06X, wherein X is the pressure in the unit of psig.

2. A non-ignitable gaseous composition consisting essentially of difluoromethane and tetrafluoroethylene, provided that when the pressure is at least 150 psig, the molar percentage of tetrafluoroethylene in said gaseous composition is no more than 111.6−0.124X.

3. A non-ignitable gaseous composition consisting essentially of difluoromethane and tetrafluoroethylene, provided that when the pressure is less than 150 psig, the molar percentage of tetrafluoroethylene in said gaseous composition is no more than 102−0.06X, wherein X is the pressure in the unit of psig.

4. The non-ignitable gaseous composition of claim 1, wherein the molar percentage of tetrafluoroethylene in said gaseous composition is no more than 68.2, and said pressure is no more than 350 psig, provided that said gaseous composition contains no catalysts.

5. The non-ignitable gaseous composition of claim 1, wherein the molar percentage of tetrafluoroethylene in said gaseous composition is no more than 77.8, and said pressure is no more than 250 psig, provided that said gaseous composition contains no catalysts.

6. The non-ignitable gaseous composition of claim 1, wherein the molar percentage of tetrafluoroethylene in said gaseous composition is no more than 93, and said pressure is no more than 150 psig, provided that said gaseous composition contains no catalysts.

7. The non-ignitable gaseous composition of claim 1, wherein the molar percentage of tetrafluoroethylene in said gaseous composition is no more than 99, and said pressure is no more than 50 psig, provided that said gaseous composition contains no catalysts.

8. A process comprising: pre-mixing difluoromethane with tetrafluoroethylene to form the composition of claim 1, provided that when the pressure is at least 150 psig, the molar percentage of tetrafluoroethylene in the mixture is no more than 111.6−0.124X, and that when the pressure is less than 150 psig, the molar percentage of tetrafluoroethylene in the mixture is no more than 102−0.06X, wherein X is the pressure in the unit of psig.

9. The process of claim 6, wherein the molar percentage of tetrafluoroethylene in the mixture is no more than 68.2, and the pressure is no more than 350 psig.

10. The process of claim 6, wherein the molar percentage of tetrafluoroethylene in the mixture is no more than 77.8, and the pressure is no more than 250 psig.

11. The process of claim 6, wherein the molar percentage of tetrafluoroethylene in the mixture is no more than 93, and the pressure is no more than 150 psig.

12. The process of claim 6, wherein the molar percentage of tetrafluoroethylene in the mixture is no more than 99, and the pressure is no more than 50 psig.

13. A composition consisting essentially of:
    (a) tetrafluoroethylene and
    (b) difluoromethane; wherein the difluoromethane is present in an effective amount to form an azeotropic combination with the tetrafluoroethylene.

* * * * *